(12) United States Patent
Takei (10) Patent No.: US 6,406,497 B2
(45) Date of Patent: Jun. 18, 2002

(54) ARTIFICIAL KNEE JOINT (75) Inventor: Tsunenori Takei, Nagano (JP)

(73) Assignees: Tsunenori Takei, Nagano; Nakashima Propeller Co., Ltd., Okayama; Hajime Yamada, Nagano, all of (JP)

( * ) Notice: Subject to any disclaimer, the term of this patent is extended or adjusted under 35 U.S.C. 154(b) by 0 days.

(21) Appl. No.: 09/907,792

(22) Filed: Jul. 18, 2001

(30) Foreign Application Priority Data

Jul. 19, 2000 (JP) ..................................... 2000-218220

(51) Int. Cl.[7] ................................................ A61F 2/38
(52) U.S. Cl. ................................. 623/20.31; 623/20.27
(58) Field of Search ........................... 623/20.24, 20.27, 623/20.31, 20.32

(56) References Cited

U.S. PATENT DOCUMENTS

| | | | | | |
|---|---|---|---|---|---|
| 4,261,064 A | * | 4/1981 | Helfet | ...................... | 623/20.27 |
| 5,059,216 A | * | 10/1991 | Winters | .................... | 623/20.27 |
| 5,282,870 A | * | 2/1994 | Moser | ...................... | 623/20.27 |
| 5,702,458 A | * | 12/1997 | Burstein | .................. | 623/20.27 |
| 5,728,162 A | * | 3/1998 | Eckhoff | ................... | 623/20.27 |
| 6,152,960 A | * | 11/2000 | Pappas | ..................... | 623/20.31 |
| 6,264,697 B1 | * | 6/2001 | Walker | ..................... | 623/20.27 |
| 6,325,828 B1 | * | 12/2001 | Dennis | ..................... | 623/20.14 |

* cited by examiner

*Primary Examiner*—Michael J. Milano
(74) *Attorney, Agent, or Firm*—Koda & Androlia (57) ABSTRACT

An artificial knee joint comprising: a femoral component comprising a femoral condylar portion made of a medial condylar section and a lateral condylar section which extend in an anteroposterior direction of the knee joint and have convex exterior surfaces, and a tibial component comprising a tibial condylar portion made of a medial condylar section and a lateral condylar section which extend in an anteroposterior direction of the knee joint and have concave interior surfaces so as to slidably receive the medial and lateral condylar sections of the fermoral condylar portion therein; and a space between the respective medial and lateral condylar sections of the femoral condylar portion and of the tibial condylar portion being formed so as to be gradually narrower toward the rear side of the knee joint, thus forming a "rear-in" configuration.

16 Claims, 8 Drawing Sheets

REAR

FRONT

ARTIFICIAL KNEE JOINT

BACKGROUND OF THE INVENTION

1. Field of the Invention

The present invention relates to an artificial knee joint which is used as a replacement of a biological knee joint.

2. Prior Art

In cases where a knee joint has ceased to function as a result of deformative joint disorders, rheumatism or external injury, etc., this knee joint is replaced by an artificial knee joint.

Such an artificial knee joint is substantially comprised of a femoral component in which two protruding surfaces, i.e., medial and lateral protruding surfaces, are joined in a front and back relationship to form a femoral condylar portion, and a tibial component in which recessed surfaces that support the femoral condylar portion so that the femoral condylar portion is capable of a sliding movement and a rolling movement are joined in a front and back relationship to form a tibial condylar portion. In this case, the femoral condylar portion has an medial condylar section and an lateral condylar section, and both of these portions are formed so that the Trajectory connecting the lowest points of the two portions constitutes an approximate circular-arc curve in two dimensions as seen in the side view. In a conventional artificial knee joint, imaginary extended lines of this approximate circular-arc curve in the anteroposterior direction are set parallel to each other.

This parallel setting sets limitations on the region of possible movement of the artificial knee joint. In particular, it is difficult to achieve maximum flexion. Examples of the deleterious effects of such a construction may be cited as follows:

1. The tibial condylar portion that supports the femoral condylar portion forms an elliptical groove that has its long axis in the anteroposterior direction as seen in a plan view. The femoral condylar portion rotates while sliding and rolling through this elliptical groove, thus allowing flexion of the knee. In this case, the femoral condylar portion is contained within the vertically projected plane of the tibial condylar portion, and does not protrude from this plane in extension. However, since the center of rotation of the femoral condylar portion moves to the rear as the angle of flexion increases, the femoral condylar portion protrudes from the vertically projected plane of the elliptical surface of the tibial condylar portion. Since the edge of the femoral condylar portion, and especially the posterior portion, contacts the running part of the hamstring on both the medial and lateral, this protrusion of the femoral condylar portion interferes with the normal tension of the hamstring, and therefore impedes flexion.

2. In a biological knee joint, the tibial condylar portion is more or less planar in the anteroposterior direction, and the attitude of the femur during flexion is controlled by the anterior and posterior cruciate ligaments. More specifically, the posterior cruciate ligaments gradually extend up to a flexion angle of approximately 60°, and then remain more or less fixed, so that the attitude is controlled. In an artificial knee joint, on the other hand, the side-surface shape of the tibial condylar portion is formed with the standing position of 0° as the deepest point, and with recessed shapes showing the shape of a "ship hull" before and after this deepest point, so that smooth rotation of the femoral condylar portion is achieved. In this case as well, a semi-constrained type configuration in which the curvature radius of the recessed shapes of the tibial condylar portion is greater than the curvature radius of the protruding shapes of the femoral condylar portion is most common. Consequently, as the femoral condylar portion bends, the position of the contact surface with the tibial condylar portion gradually becomes higher, which differs from the movement of a biological knee joint. Accordingly, when the cruciate ligaments are retained, the extension of these ligaments becomes excessive, so that attitude control becomes difficult to achieve. Even in cases where the cruciate ligaments are excised, the extension of the medial and lateral collateral ligaments is excessive, and smooth flexion is impeded.

3. In order for the femoral condylar portion to obtain a large flexion angle, the condylar portion must be correspondingly extended upward and to posterior. However, in the case of parallel setting that requires a wide area, this interferes with ligaments and tendons that are present in the upper posterior area, so that this extension cannot be made very long. As a result, the flexion angle in a conventional artificial knee joint is limited to approximately 110 to 120°. However, flexion of approximately 150° is necessary for, for instance, an upright sitting on a plane surface or a Japanese-style sitting position, etc.

4. In a biological knee joint, the smoothness of flexion is aided by an internal and external axial rotation movement of the femur as the flexion angle increases. However, if the femoral condylar portion and tibial condylar portion are set parallel to each other, this internal and external axial rotation movement is restricted. In other words, when the flexion angle increases, the femoral condylar portion leaves the recessed groove of the tibial condylar portion and is lifted upward, so that normal axial rotation is hindered, and the cruciate ligaments and medial and lateral collateral ligaments are excessively extended. Thus, smooth flexion and axial rotation are difficult.

SUMMARY OF THE INVENTION

The object of the present invention is to solve the above problems.

The above object is accomplished by a unique structure for an artificial knee joint in which the knee joint comprises:

a femoral component comprising a femoral condylar portion that consists of an medial condylar section and an lateral condylar section, the medial and lateral condylar sections extending in a anteroposterior direction of the knee joint and have protruding exterior surfaces; and a tibial component comprising a tibial condylar portion that consists of an medial condylar section and lateral condylar section, the medial and lateral condylar sections extending in a anteroposterior direction of the knee joint and have recessed interior surfaces so as to support the medial and lateral condylar sections of the femoral condylar portion in such a manner that the medial and lateral condylar sections of the femoral condylar portion can make sliding and rolling movements; and wherein a spacing between the respective medial condylar sections and lateral condylar sections of the femoral condylar portion and of the tibial condylar portion is formed so as to be gradually narrower toward the posterior side of the knee joint, thus forming a "rear-in" configuration.

With the respective medial condylar sections and lateral condylar sections of the femoral condylar portion and tibial condylar portion formed in a "rear-in" configuration, which is a characterizing feature of the present invention, the following advantages are obtained:

1. Since the spacing of the femoral condylar portions is formed in a "rear-in" configuration, the spacing (distance of separation) of the femoral medial condylar section and lateral condylar section decreases as the flexion angle increases. Accordingly, even in the case of a high degree of flexion, the femoral condylar portion does not protrude from the tibial condylar portion, but remains within the vertically projected plane of the tibial condylar portion. As a result, there is no interference with the hamstring or impairment of the normal tension of the hamstring.

2. This means that the degree to which the femoral condylar portion is elevated from the tibial condylar portion is small even in the case of a high degree of flexion, so that the tension of the collateral ligaments is not extended, thus allowing smooth flexion.

3. In the "rear-in" configuration as well, the load applied to the knee joint during flexion is applied to the positions of the centers of gravity of the medial and lateral condylar sections. Accordingly, when a large flexion angle is adopted, the center of gravity move to the medial or lateral of the top line that connects the lowest points of the condylar portions, and the curvature radius is correspondingly decreased, because the mediolateral radius of the femoral component portions are smaller than the anteroposterior. If the curvature radius is small, the amount of displacement of the center of rotation is also correspondingly decreased, so that a large flexion angle can be obtained with a small displacement, thus allowing a high degree of flexion. Furthermore, if the rotational radius is small, flexion can be accomplished by means of a light force.

4. With the "rear-in" configuration, the axial rotation of the femur about the axis of the tibia can also be accomplished by means of a light force, since the rotational radius is reduced. Furthermore, the joint is stable with no oscillation, etc. Accordingly, the flexion action is aided, and a large flexion angle can be obtained.

DETAILED DESCRIPTION OF THE INVENTION

An embodiment of the present invention will be described below with reference to the attached figures.

The artificial knee joint is comprised of a pair of femoral component 1 and tibial component 2. Of these components, the femoral component 1 is constructed from a biocompatible metal such as a titanium alloy, etc. and is mounted on the distal end of the femur.

The outline of this femoral component 1 is substantially circular when viewed from the side. A high floor section 3 that extends horizontally in the anteroposterior direction is formed in the center of the interior of the femoral component 1, and low floor sections 4 are formed on both sides of this high floor section 3. Front walls 5 and rear walls 6 are formed in upright positions on the front and rear ends of the floor sections 3 and 5.

A pocket 7 is formed in the center of the under side of the high floor section 3. The pocket 7 is oriented in the anteroposterior direction. The outlines of the areas on the left and right of the pocket 7 are formed as protruding surfaces that protrude downward or outward. These protruding or outwardly curved surfaces are joined in the front and rear at a specified curvature radius R (see FIG. 3), thus forming a femoral condylar portion 8 consisting of an medial condylar section 8a and lateral condylar section 8b. In other words, the femoral component 1 comprises, along with the high floor section 3, low floor sections 4, and front walls 5, etc., a femoral condylar portion 8 that consists of a pair of condylar sections 8a and 8b; and each one of the condylar sections 8a and 8b is formed so that the exterior surface are curved in the anteroposterior direction as seen from FIG. 5 (only the exterior surface being shown). In addition, each of the condylar sections 8a and 8b has a protruding or convex surface with respect to the width direction of the condylar sections 8a and 8b so that a curved ridge T extends at substantially the center thereof as seen in FIG. 6. Also, the spacing in the femoral condylar portion 8, i.e., the spacing between the medial condylar section 8a and lateral condylar section 8b, is made narrower or gradually decreases toward the back or rear side of the femoral component 1 as seen from FIG. 6. In other words, this spacing is formed in a "rear-in" configuration.

Figure 1:
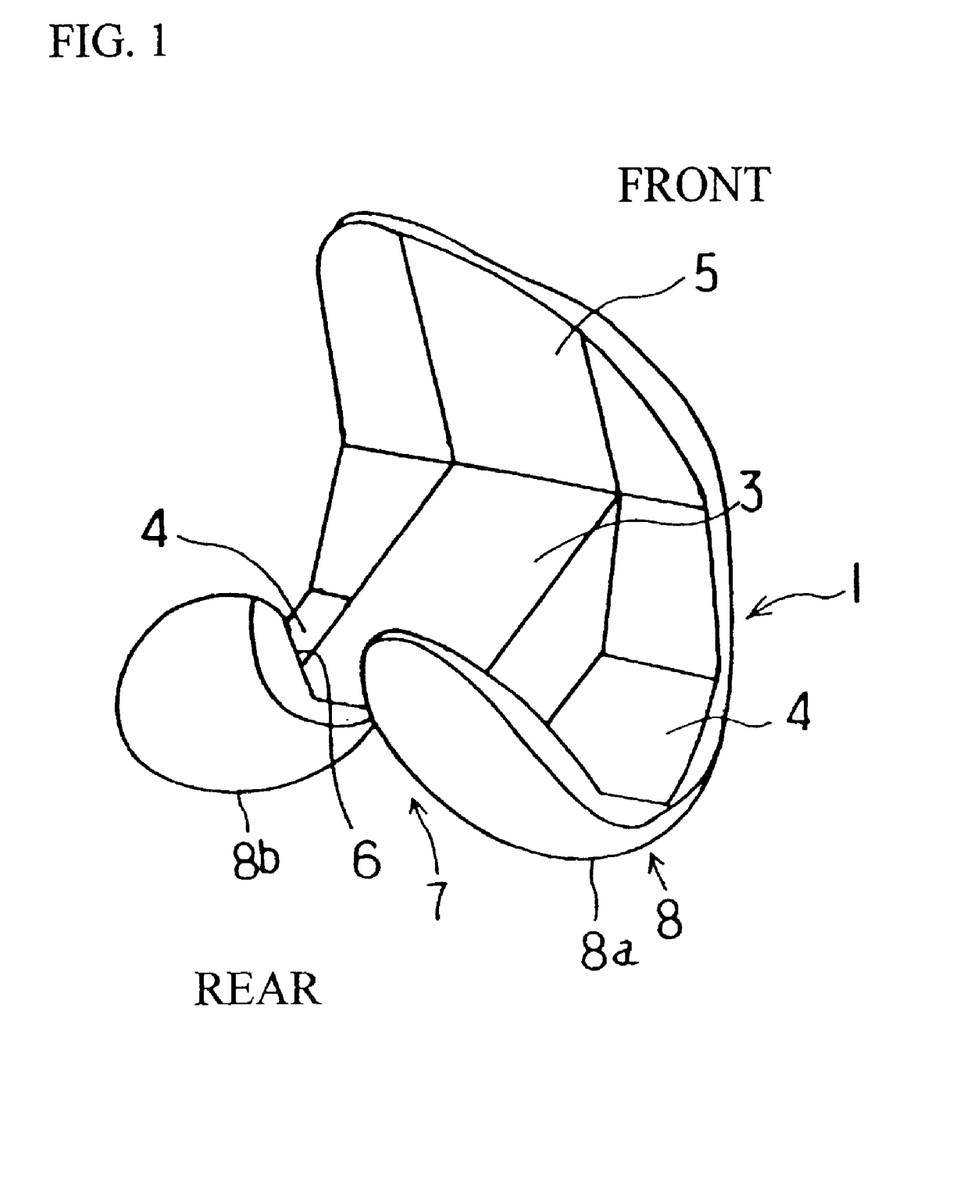
FIG. 1 is a perspective view of a femoral component illustrating one embodiment of the present invention.
Figure 2:
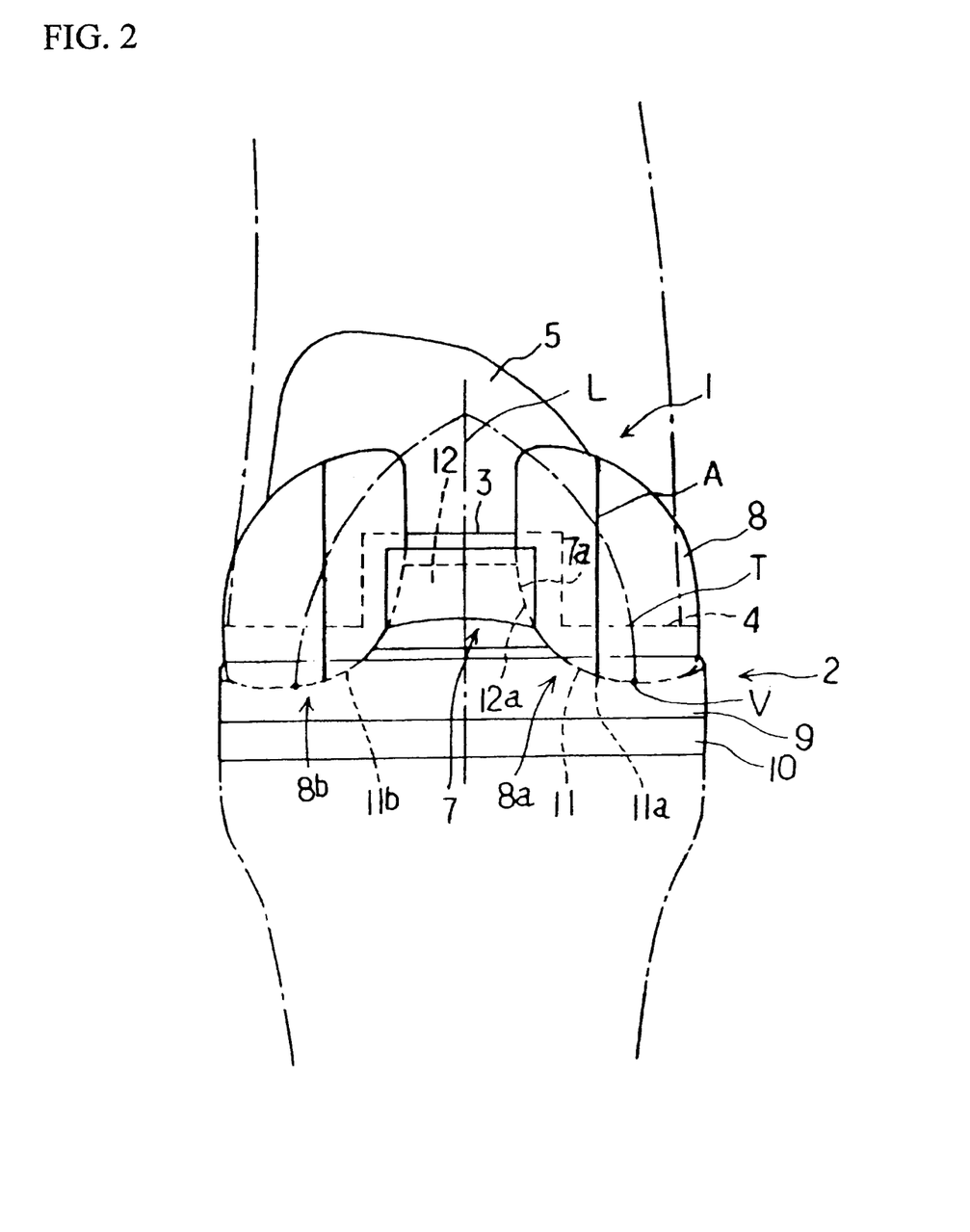
FIG. 2 is a back view of the mounted state of an artificial knee joint illustrating one embodiment of the present invention.

In this "rear-in" configuration, it is desirable that both the medial condylar section 8a and the lateral condylar section 8b be arranged symmetrically in a "rear-in" configuration with respect to the centerline L. The line connecting the respective lowest points or the outermost points on the medial condylar section 8a and lateral condylar section 8b form a circular arc when viewed from behind as shown in FIG. 2. This circular arc (that correspond to the ridge line T) is set so that the imaginary lines extended from the ridgeline T intersect on the centerline L of the femoral component 1 as seen from FIG. 2.

On the other hand, the tibial component 2 is comprised of a plate 9 and a base 10 that supports the plate 9. The plate 9 supports the femoral condylar portion 8 of the femoral component 1 so that the femoral condylar portion 8 is capable of making a sliding movement and a rolling movement. The plate 9 is constructed from an ultra-high-molecular-weight polyethylene for medical use, etc.

More specifically, a pair of curved, recessed or concave surfaces that correspondingly receive the respective protruding surfaces or the outwardly curved exterior surface of the respective medial and lateral condylar section 8a and 8b of the femoral condylar portion 8 are formed so as to extend anterior to posterior on the upper surface of the plate 9 with a specified curvature radius S. The recessed surfaces that thus extend in the anteroposterior direction form a pair of medial condylar section 11a and lateral condylar section 11b. The medial condylar section 11a and lateral condylar section 11b form a tibial condylar portion 11. Accordingly, when the recessed surfaces of the medial condylar section 11a and lateral condylar section 11b are viewed from above, they show a "kidney bean shape" with convergence toward the back side, thus corresponding to the curved shape of the medial and lateral condylar sections 8a and 8b of the femoral component 1. In other words, the plate 9 that is a part of the tibial component 2 is formed with the tibial condylar portion 11 that is comprised of the medial condylar section 11a and the lateral condylar section 11b; and each one of the medial condylar section 11a and the lateral condylar section 11b is formed so that the interior surface thereof is curved in the anteroposterior direction (in view of FIG. 5) and also has a concave shape with a curved bottom line V at the center thereof so as to correspond to the curved ridge T of the medial and lateral condylar sections 8a and 8b of the femoral condylar portion 8 of the femoral component 1.

The curvature radius S of the tibial condylar portion 11 of the tibial component 2 is set so as to be larger than the curvature radius R of the femoral condylar portion 8 of the femoral component 1. However, substantially a curved bottom line V in the rear half of the tibial component 2 is formed substantially flat so as to have no curvature.

The spacing of the tibial condylar portion 11, i.e., the spacing between the medial condylar section 11a and lateral condylar section 11b, is also formed in a "rear-in" configuration toward the rear side, in the same manner as the spacing of the femoral condylar portion 8. A post 12 which interacts with the pocket 7 of the femoral component 1 is disposed in an upright position between the medial condylar section 11a and lateral condylar section 11b. The detail of this post 12 will be described later.

The base 10, that is as described above a part of the tibial component 2, is formed from a titanium alloy, etc., and is fastened to the proximal end of the tibia. Since the positions of the plate 9 and base 10 must not shift, mutually interlocking recesses and projections, etc. are formed in the joining surfaces of these components, so that the fastening of the plate 9 and base 10 is reinforced.

The artificial knee joint consisting of the above-described femoral component 1 and tibial component 2 is mounted on the knee joint by a surgical procedure. In this case, the femoral component 1 is mounted on the femur so that the distal end of the femur is shaped and the front and rear portions of the femur are respectively inserted between the front walls 5 and rear walls 6 of the femoral component 1, while the medial and lateral portions of the femur are set on the low floor sections 4 straddling the high floor section 3. Meanwhile, the mounting of the tibial component 2 on the tibia is accomplished by flattening the proximal end of the tibia and fastening the base 10 to the end surface. In this case, a stem 13 can be provided to protrude from the undersurface of the base 10. Fastening of such a stem 13 into the tibia reinforces the mounting of the tibial component 12.

A description will be given with reference to the shape of the pocket 7 that is formed between the medial condylar section 8a and lateral condylar section 8b of the femoral condylar portions 8 and the shape of the post 12 that is formed between the medial condylar section 11a and lateral condylar section 11b of the tibial condylar portions 11.

First, when the femoral condylar portion 8 is mounted on the upper surface of the tibial condylar portion 11, as seen in FIG. 2 that is a rear view, the pocket 7 has is narrower at an upper area thereof and wider at an lower area thereof and has side inclined surfaces 7a that run along the curvature of the protruding surfaces of the femoral condylar portion 8. The side surface portions 12a of the post 12 are in contact with the side inclined surfaces 7a. Furthermore, as seen in from FIG. 3 that is a side view, a funnel-shaped dropping portion 7b is formed in front of the pocket 7, and a hemispherical cam 14 is formed in the rear side of the dropping portion 7b with a foot portion 7c disposed in a high position interposed.

Figure 3:
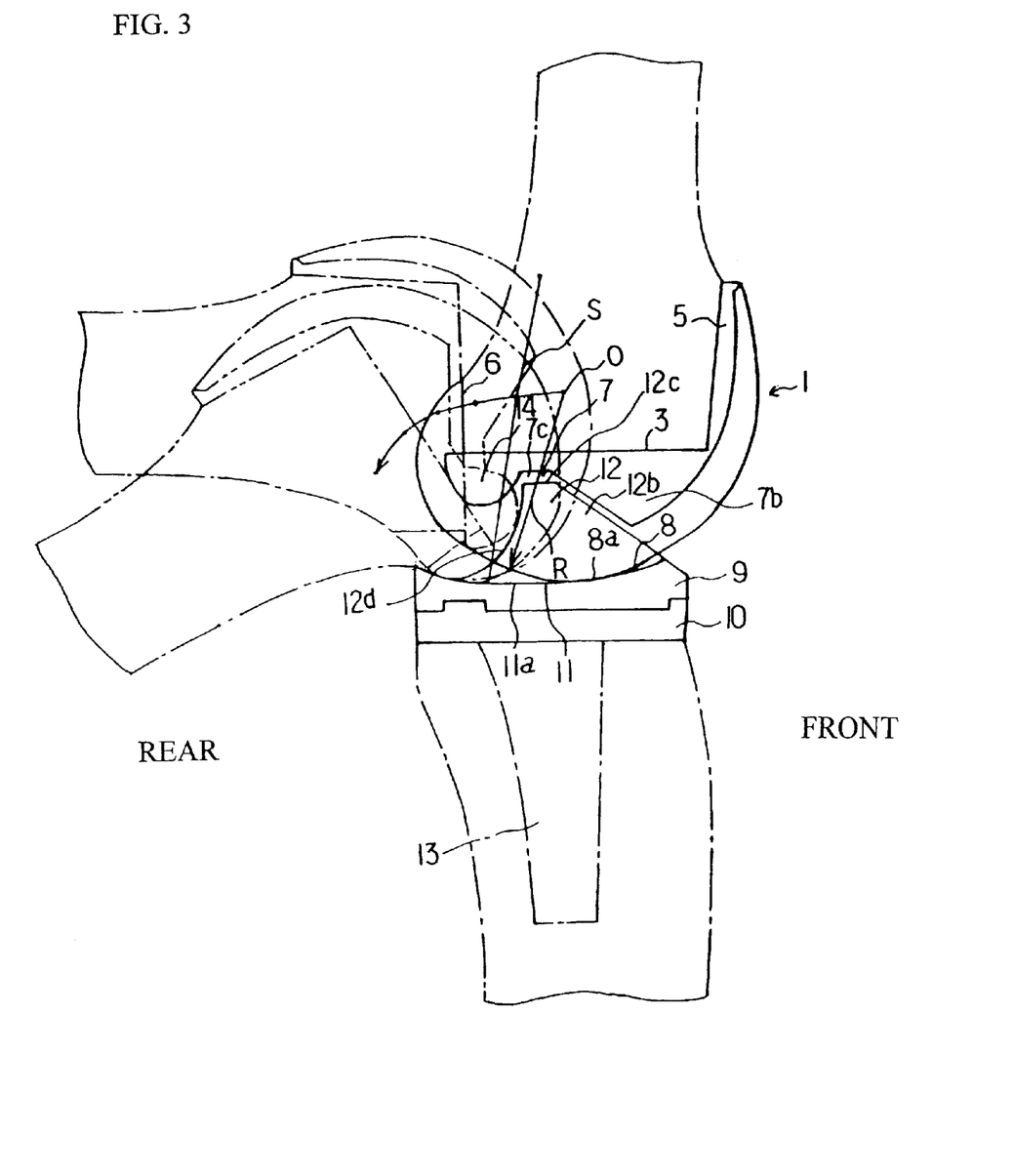
FIG. 3 is a side view of the mounted state of an artificial knee joint illustrating one embodiment of the present invention.

Furthermore, the post 12 has a front inclined portion 12b and a top portion 12c that correspond to the shapes of the dropping portion 7b and foot portion 7c with a fixed gap left between the front inclined portion 12b and the top portion 12c. Moreover, the post 12 also has a rear inclined portion 12d which is hollowed out in a recessed surface shape from the top portion 12c.

With the structure described above, the operation that makes flexion of the knee will be described with reference to FIG. 3. When the femoral component 1 and the tibial component 2 are caused to rotate relative to each other in FIG. 3, the femoral condylar portion 8 rotates and moves rearward with respect to the tibial condylar portion 11 (when the tibial side is viewed as being fixed). In this case, if there were no sliding of the femoral condylar portion 8 relative to the tibial condylar portion 11, the femoral condylar portion 8 would soon fall out of the tibial condylar portion 11. Accordingly, the femoral condylar portion 8 rolls while appropriately sliding forward. In any case, however, the center of rotation O of the femoral condylar portion 8 moves rearward. The cam 14 formed in the pocket 7 and the rear inclined portion 12d of the post 12 that acts on the cam 14 control the sliding movement and rolling movement during this flexing operation, so that the attitudes of the sliding movement and rolling movement are stabilized.

In concrete terms, the femoral condylar portion 8 rotates relative to the tibial condylar portion 11 while a state in which these portions are in contact is maintained (i.e., while forward movement is restricted). This rotation is performed from a standing position of 0° to a Japanese-style upright sitting position of 150°. Accordingly, the shapes of the cam 14 and rear inclined portion 12d are designed in order to make this possible. Furthermore, contact between the side surface portions 12a of the post 12 and the side inclined surfaces 7a of the pocket 7 is maintained during this rotation, so that a tight movement with the post 12 as a pivot is guaranteed, and so that the contact surface area is increased, thus lowering the surface pressure, so that wear, etc., is reduced.

In the present invention, the femoral condylar portion 8 and tibial condylar portion 11 are both formed in a "rear-in" configuration as shown in FIG. 2. As a result, the top or ridge line T of the convex surfaces of the femoral condylar portion 8 and the bottom line V of the concave surfaces of the tibial condylar portion 11 are correspondingly formed in a "rear-in" configuration.

Figure 4:
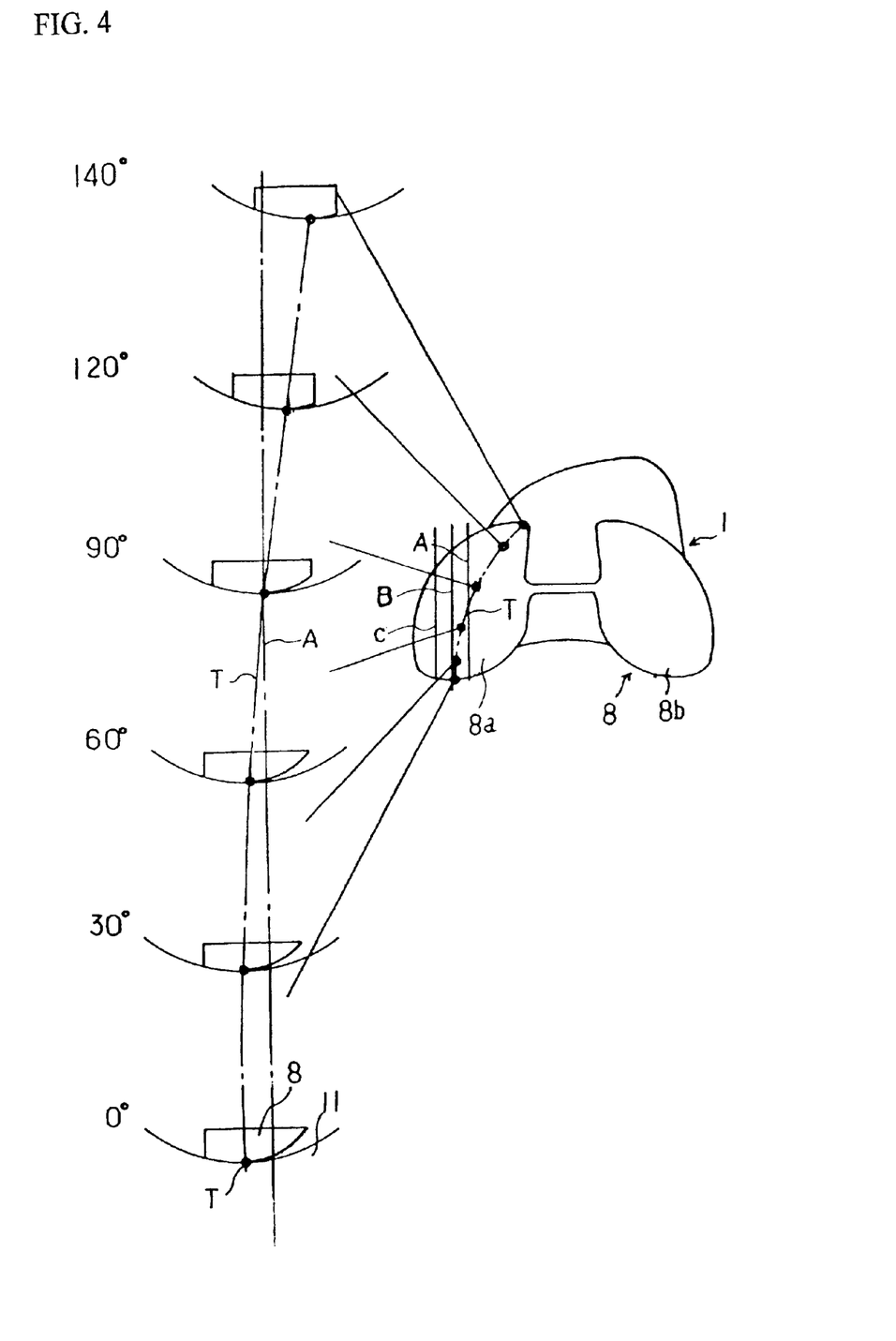
FIG. 4 is an explanatory back view of a femoral component illustrating one embodiment of the present invention.
Figure 5:
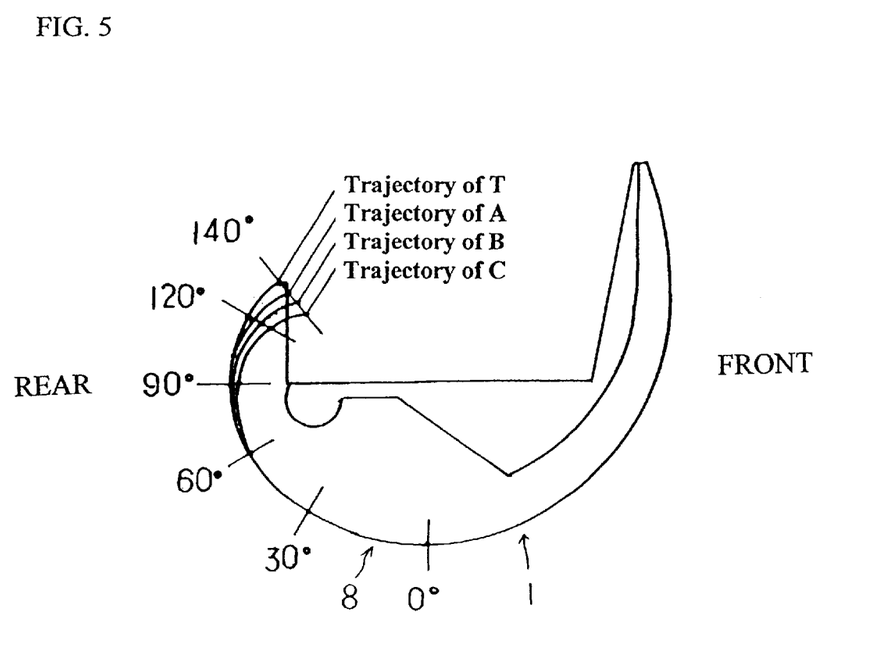
FIG. 5 is an explanatory side view of a femoral component illustrating one embodiment of the present invention.
Figure 6:
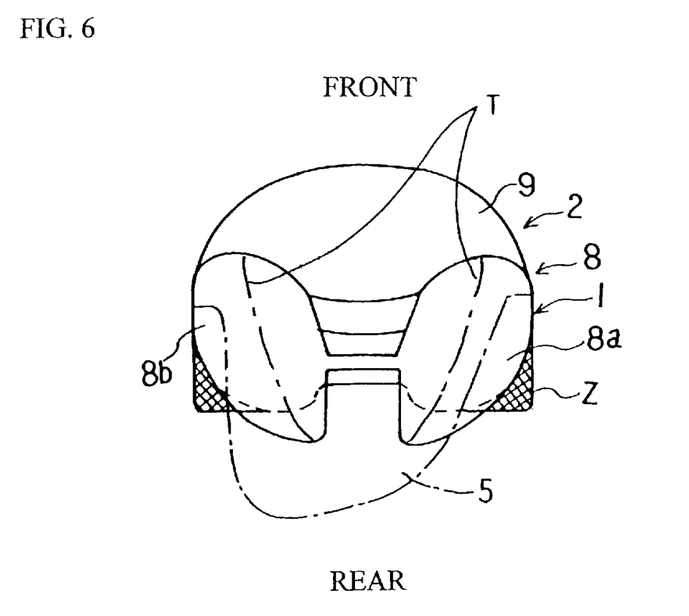
FIG. 6 is a plan view of the mounted state of an artificial knee joint illustrating one embodiment of the present invention.

FIG. 4 is an explanatory rear view of the femoral component 1 which shows the state of contact between the femoral condylar portion 8 and tibial condylar portion 11 according to the flexion angle, and FIG. 5 is an explanatory side view thereof. Here, the load is applied to the knee joint parallel to the axes of the bones, and the direction of the load is not affected by the flexion angle. Accordingly, the line A that connects the maximum load points (centers of gravity) is more or less parallel, thus differing from the top line T and bottom line V, which are in a "rear-in" configuration.

Accordingly, in the rear half, this line A is naturally positioned to the outside of the top line T, etc. However, when the femoral condylar portion 8 and tibial condylar portion 11 rotate, the establishment of the relationship between the femoral condylar portion 8 and the tibial condylar portion 11 depends on the above-described line A as described above. Accordingly, if this line A is positioned to the outside of the top line T, etc., the actual rotational radius is correspondingly decreased, so that a large flexion angle can be obtained with a small displacement, and so that only a small force is required for flexion. At the same time, in the case of internal rotation or external rotation, since the rotational radius of this axial rotation is also decreased, there is no lateral oscillation, etc., and smooth rotation can be obtained with a light force. Furthermore, since the curvature radius S of the tibial condylar portion 11 is set at a large value in the latter half, upward floating of the femoral condylar portion 8 during flexion is reduced, so that a flexing action with little vertical movement can be obtained, thus allowing a high degree of flexion.

The above-described line A is set at a distance of 20 mm from the center of the medial condylar section 8a and lateral condylar section 8b. However, a line B with a distance of 23.5 mm from the center and a line C with a distance of 27 mm from the center were experimentally set in FIG. 4. The trajectories of the respective lines A through C that were observed when the joint was flexed are shown in FIG. 5. It is seen from these results that the rotational radius in the case of an increased flexion angle decreases with an increase in the distance from the center. Accordingly, it may be said that as line A, which constitutes the maximum load point, is separated further to the outside of the top line T (or in other words, as the top line T is set further to the inside of line A), the flexuosity of the joint increases. Accordingly, this top line T is set in accordance with the conditions of the respective patients (age, symptoms, desires and living habits).

FIG. 6 is a plan view showing a state in which the femoral condylar portion 8 is flexed 90° with respect to the tibial condylar portion 11.

It should be noted that if the femoral condylar portion 8 and the tibial condylar portion 11 are thus formed with a "rear-in" structure, the femoral condylar portion 8 will not protrude from the vertically projected plane of the plate 9 formed by the tibial condylar portion 11 even if the femoral condylar portion 8 is flexed to a great degree. If the femoral condylar portion 8 and the tibial condylar portion 11 are set parallel as in the conventional joint, the femoral condylar portion 8 will protrude from the plate 9 as indicated by the shaded portion Z as a result of the center of rotation O moving to a rear side. If this happens, there will be interference with the hamstring, etc., as described above.

Figure 7:
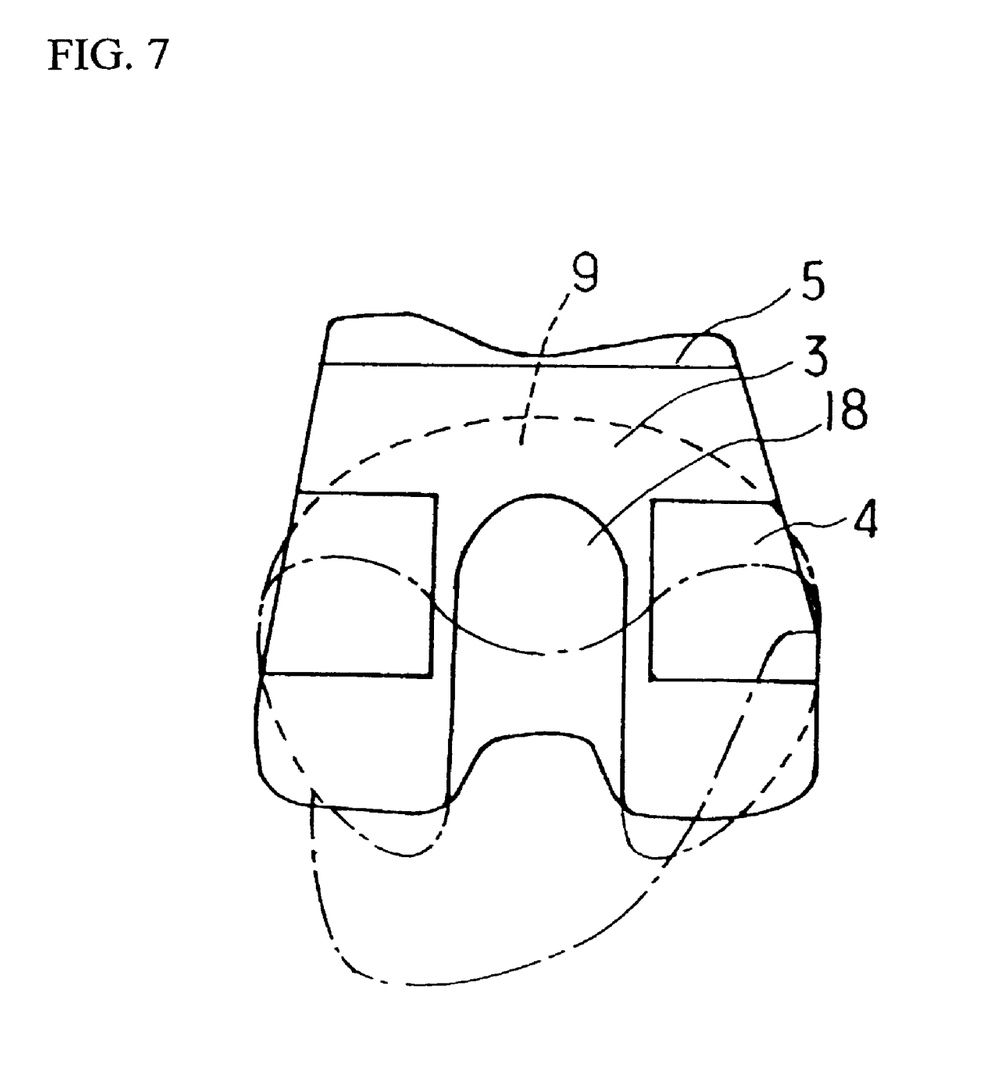
FIG. 7 is a plan view of the mounted state of an artificial knee joint illustrating another embodiment of the present invention.
Figure 8:
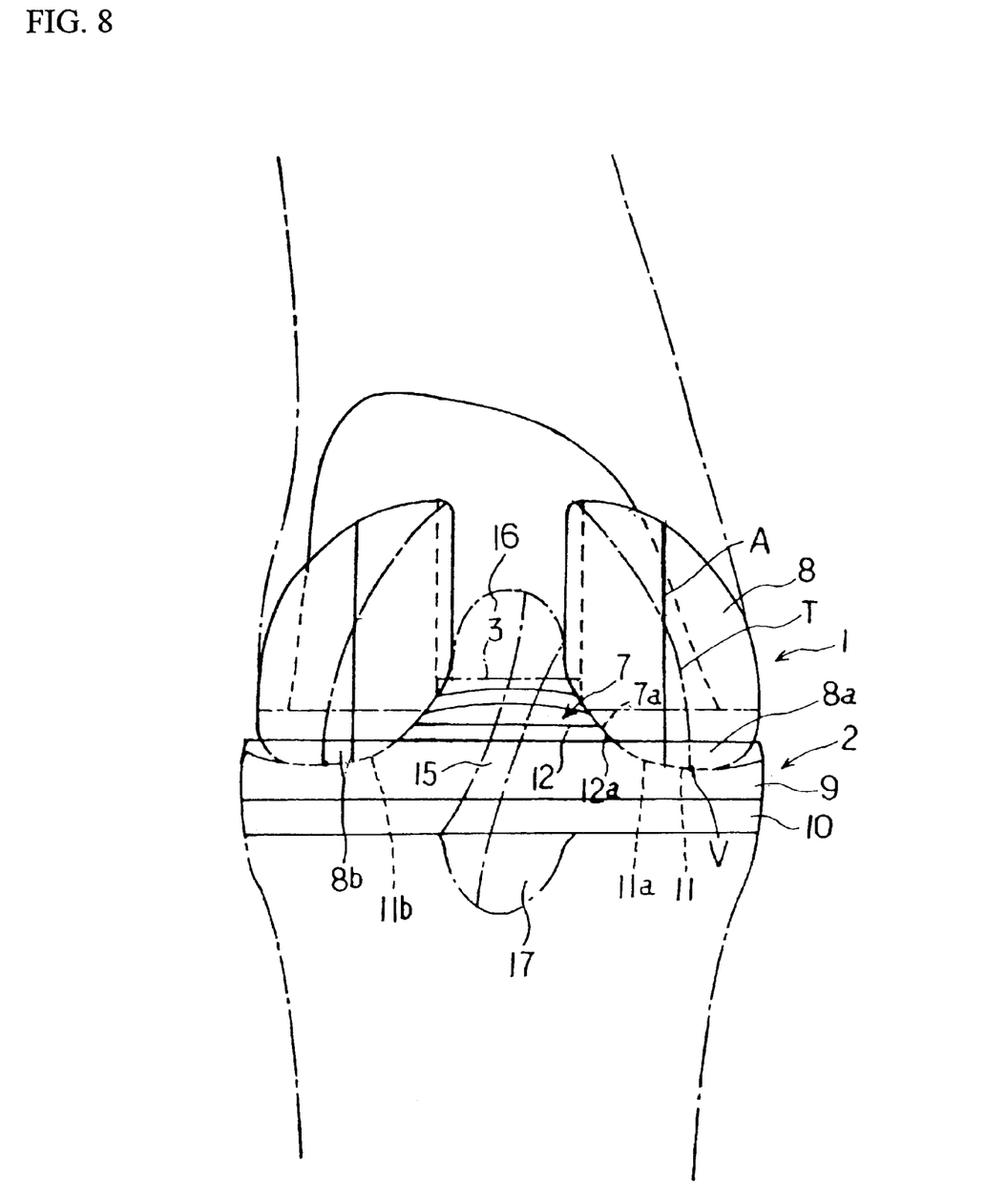
FIG. 8 is a back view of the mounted state of an artificial knee joint illustrating another embodiment of the present invention.
Figure 9:
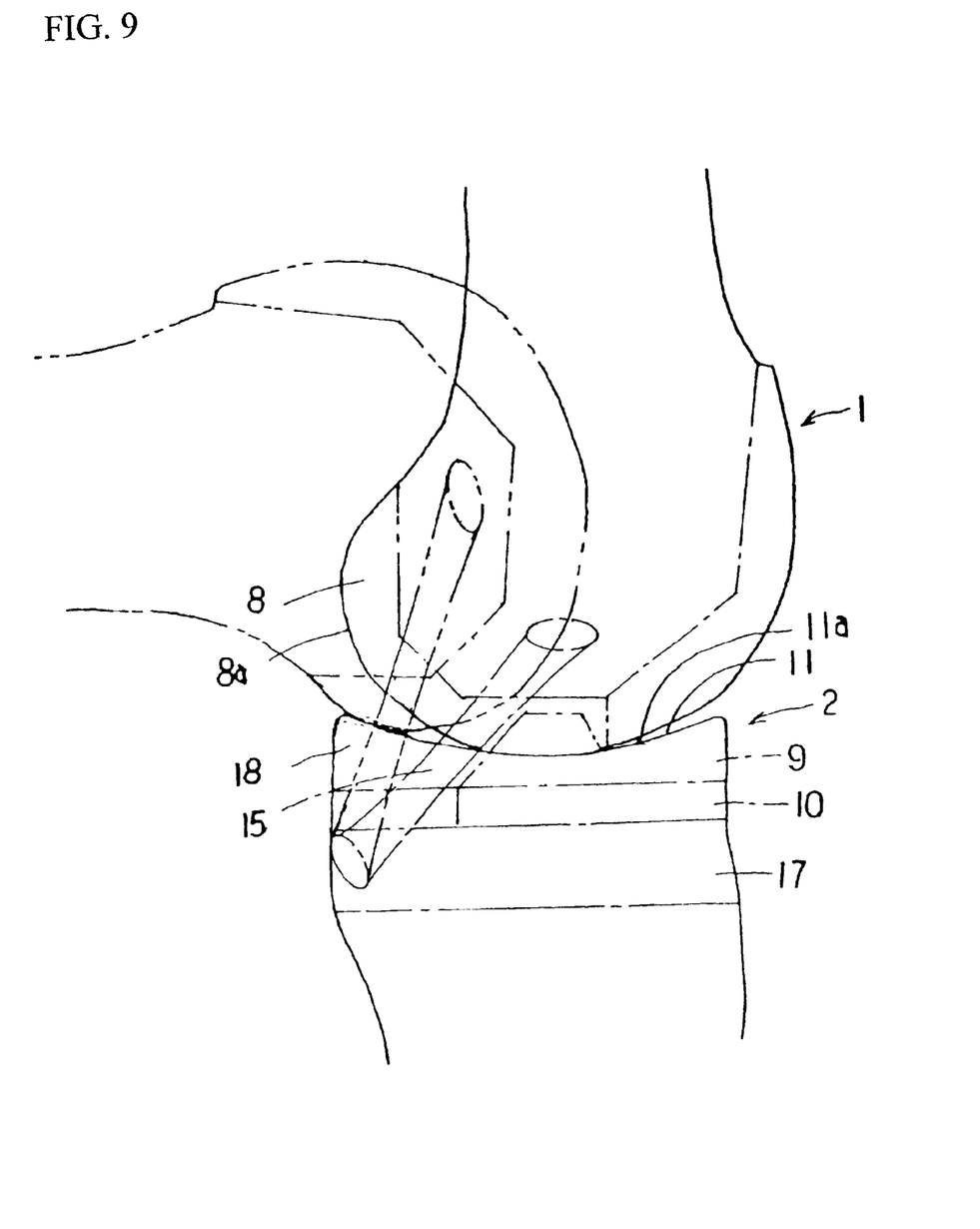
FIG. 9 is a side view of the mounted state of an artificial knee joint illustrating another example of the present invention.

The above description is made for an artificial knee joint which is applied to a knee joint from which the cruciate ligaments have been excised. However, this artificial knee joint can also be mounted on a knee joint in which there has been little damage to the cruciate ligaments, and especially a knee joint in which a relatively undamaged posterior cruciate ligament is retained. FIG. 7 is a plan view showing the mounting of an artificial knee joint of this type on the knee. FIG. 8 is a rear view thereof, and FIG. 9 is a side view thereof.

The basic structures of both the femoral component 1 and the tibial component 2 are unchanged from the previous embodiment. However, in an artificial knee joint shown in FIGS. 7 through 9, attitude control during rotation is accomplished by means of the posterior cruciate ligament 15. Accordingly, a recess 16 between the living femoral condyles and a recess 17 between the tibial condyles, through which the posterior cruciate ligament 15 passes, remain in this artificial knee joint, and the shaping of the distal end of the femur and proximal end of the tibia on which this joint is mounted is performed accordingly.

In addition, no cam 14 or rear inclined portion 12d of the post 12 is installed. Also, a groove 18 that allows the passage of the posterior cruciate ligament 15 is cut out in the high floor section 3 between the femoral condylar portion 8 from a rear side. Here, in regard to the post 12 located between the medial condylar section 11a and lateral condylar section 11b of the tibial condylar portions 11, a post that is low in height and its rear half is cut away to an extent that prevents interference with the posterior cruciate ligament 15 is formed. As in the previous embodiment, the side inclined surfaces 7a of the pocket 7 contact this post 12. Furthermore, the femoral condylar portion 8 and tibial condylar portion 11 have a "rear-in" structure, and the behavior during flexion and internal and external axial rotation is also the same as that in the previous embodiment.

As seen from the above, in the artificial knee joint of the present invention, the femoral condylar portion and tibial condylar portion are formed in a "rear-in" configuration. As a result, stable flexion with smaller vertical movement and lateral oscillation can be obtained over a large angle by means of a light force. At the same time, there is no damage to surrounding ligaments or tendons even in the case of a high degree of flexion.

What is claimed is:

1. An artificial knee joint comprising:
   a femoral component comprising a femoral condylar portion that consists of an medial condylar section and an lateral condylar section, said medial condylar section and lateral condylar section extending in an anteroposterior direction of said knee joint and have protruding exterior surfaces; and
   a tibial component comprising a tibial condylar portion that consists of a medial condylar section and a lateral condylar section, said medial condylar section and lateral condylar section extending in an anteroposterior direction of said knee joint and have recessed interior surfaces so as to support therein said medial condylar section and lateral condylar section of said femoral condylar portion, said medial condylar section and lateral condylar section of said femoral condylar portion being capable of making a sliding movement and rolling movement, wherein
   a spacing between respective medial condylar sections and lateral condylar sections of said femoral condylar portion and of said tibial condylar portion is formed so as to be gradually narrower toward a rear side of said knee joint.

2. The artificial knee joint according to claim 1, wherein both of said medial condylar sections and lateral condylar sections of said femoral condylar portion and of said tibial condylar portion are symmetrically formed in a rear-in configuration with respect to centerlines of said medial condylar sections and lateral condylar sections of said femoral condylar portion and of said tibial condylar portion.

3. The artificial knee joint according to claim 1 or 2, wherein a line connecting respective lowest points of said medial condylar section and lateral condylar section of said femoral condylar portion forms substantially a circular arc as seen in a rear view, and imaginary lines extended from said circular arc intersect on a center line above upper edges of said condylar portions.

4. The artificial knee joint according to claim 1 or 2, further comprising a post which rises with inclined surfaces that have a wider lower portion as seen in a rear view, said post being disposed between said medial condylar section and lateral condylar section of said tibial condylar portion and being in contact with facing inside surfaces of said medial condylar section and lateral condylar section of said femoral condylar portion.

5. The artificial knee joint according to claim 3, further comprising a post which rises with inclined surfaces that have a wider lower portion as seen in a rear view, said post being disposed between said medial condylar section and lateral condylar section of said tibial condylar portion and being in contact with facing inside surfaces of said medial condylar section and lateral condylar section of said femoral condylar portion.

6. The artificial knee joint according to claim 1 or 2, wherein a knee joint is a joint from which cruciate ligaments have been excised, and a cam which controls an attitude during flexion of said knee by acting on a rear surface of said post is disposed between said medial condylar section and lateral condylar section of said femoral condylar portion.

7. The artificial knee joint according to claim 3, wherein a knee joint is a joint from which cruciate ligaments have been excised, and a cam which controls an attitude during flexion of said knee by acting on a rear surface of said post is disposed between said medial condylar section and lateral condylar section of said femoral condylar portion.

8. The artificial knee joint according to claim 4, wherein a knee joint is a joint from which cruciate ligaments have been excised, and a cam which controls an attitude during flexion of said knee by acting on a rear surface of said post is disposed between said medial condylar section and lateral condylar section of said femoral condylar portion.

9. The artificial knee joint according to claim 1 or 2, wherein a knee joint is a joint in which posterior cruciate ligament is retained, and an attitude during flexion is controlled by extension of said posterior cruciate ligament.

10. The artificial knee joint according to claim 3, wherein a knee joint is a joint in which posterior cruciate ligament is retained, and an attitude during flexion is controlled by extension of said posterior cruciate ligament.

11. The artificial knee joint according to claim 4, wherein a knee joint is a joint in which posterior cruciate ligament is retained, and an attitude during flexion is controlled by extension of said posterior cruciate ligament.

12. The artificial knee joint according to claim 5, wherein a knee joint is a joint in which posterior cruciate ligament is retained, and an attitude during flexion is controlled by extension of said posterior cruciate ligament.

13. The artificial knee joint according to claim 6, wherein a knee joint is a joint in which posterior cruciate ligament is retained, and an attitude during flexion is controlled by extension of said posterior cruciate ligament.

14. The artificial knee joint according to claim 7, wherein a knee joint is a joint in which posterior cruciate ligament is retained, and an attitude during flexion is controlled by extension of said posterior cruciate ligament.

15. The artificial knee joint according to claim 8, wherein a knee joint is a joint in which posterior cruciate ligament is retained, and an attitude during flexion is controlled by extension of said posterior cruciate ligament.

16. An artificial knee joint comprising:
   a femoral component that is mounted on femur and is comprised of a medial condylar section and a lateral condylar section each having an convex exterior surface, and
   a tibial component that is mounted on tibia and is comprised of a medial condylar section and a lateral condylar section each having an concave interior surface and respectively receives said medial condylar section and lateral condylar section of said femoral component so that said femoral component makes a sliding and rolling movement on said tibial component, wherein
   said medial condylar section and lateral condylar section of said femoral component are formed so as to extend from an anterior side to a posterior side of said knee joint with a spacing between said medial condylar section and lateral condylar section of said femoral component gradually decreasing toward said rear side, and
   said medial condylar section and lateral condylar of said tibial component are formed so as to extend from an anterior side to a posterior side of said knee joint with a spacing between said medial condylar section and lateral condylar of said tibial component gradually deceasing toward said rear side.

* * * * *